(12) United States Patent
Ockuly

(10) Patent No.: US 6,458,107 B1
(45) Date of Patent: Oct. 1, 2002

(54) STEERABLE CORONARY SINUS CATHETER

(75) Inventor: John D. Ockuly, Minnetonka, MN (US)

(73) Assignee: Daig Corporation, Minnetonka, MN (US)

( * ) Notice: Subject to any disclaimer, the term of this patent is extended or adjusted under 35 U.S.C. 154(b) by 0 days.

(21) Appl. No.: 09/440,631

(22) Filed: Nov. 15, 1999

Related U.S. Application Data

(63) Continuation-in-part of application No. 09/146,857, filed on Sep. 3, 1998, now Pat. No. 5,984,909, and a continuation-in-part of application No. 08/996,887, filed on Dec. 23, 1997, now Pat. No. 6,001,085, which is a continuation of application No. 08/371,849, filed on Jan. 12, 1995, now Pat. No. 5,549,581, which is a continuation of application No. 08/106,383, filed on Aug. 13, 1993, now Pat. No. 5,423,772.

(51) Int. Cl.$^7$ .............................................. A61M 25/00
(52) U.S. Cl. ........................ 604/282; 607/122; 600/381
(58) Field of Search ................................ 604/280–282; 607/119, 122, 123, 127, 128; 600/373–375, 381, 433–435

(56) References Cited

U.S. PATENT DOCUMENTS

| | | | |
|---|---|---|---|
| 4,882,777 A | | 11/1989 | Narula |
| 5,358,479 A | * | 10/1994 | Wilson |
| 5,395,329 A | | 3/1995 | Fleischhacker et al. |
| 5,423,772 A | | 6/1995 | Lurie et al. |
| 5,549,581 A | | 8/1996 | Lurie et al. |
| 5,643,231 A | | 7/1997 | Lurie et al. |
| 5,722,963 A | | 3/1998 | Lurie et al. |
| 5,779,669 A | | 7/1998 | Haissaguerre et al. |
| 5,782,828 A | | 7/1998 | Chen et al. |

* cited by examiner

Primary Examiner—Jeffrey P. Jastrzab
(74) Attorney, Agent, or Firm—Scott R. Cox

(57) ABSTRACT

A steerable catheter for insertion into the ostium of the coronary sinus in the right atria including a flexible catheter body, and a steerable catheter handle wherein the catheter body includes a generally straight proximal section, a deflectable distal section and a precurved tip portion located at a distal end of the deflectable distal section. Preferably, the precurved tip portion curves outside of a plane formed by the deflectable distal section from about 20 degrees to about 50 degrees.

16 Claims, 4 Drawing Sheets

16  FOSSA OVALIS
10  CSL STEERABLE CATHETER
12  IVC
14  OS OF CS
20  TRICUSPID VALVE
18  EUSTATION RIDGE
22  S.V.C.

16 FOSSA OVALIS
10 CSL STEERABLE CATHETER
12 IVC
14 OS OF CS
20 TRICUSPID VALVE
18 EUSTATION RIDGE
22 S.V.C.

STEERABLE CORONARY SINUS CATHETER

CROSS REFERENCE TO RELATED APPLICATION

This is a continuation-in-part application of application Ser. No. 09/146,857, filed Sep. 3, 1998, now U.S. Pat. No. 5,984,909, and application Ser. No. 08/996,887, filed Dec. 23, 1997, now U.S. Pat. No. 6,001,085, which are a continuation of application Ser. No. 08/371,849, Jan. 12, 1995, U.S. Pat. No. 5,549,581, which is a continuation of application Ser. No. 08/106,383, Aug. 13, 1993, U.S. Pat. No. 5,423,772.

BACKGROUND OF INVENTION

1. Field of Invention

This invention relates to cardiac catheters, more particularly, this invention relates to a steerable catheter with a precurved tip portion designed for use in the coronary sinus of a human heart.

2. Prior Art

Catheters have been in use in medical procedures for many years. For example, they can be used to convey an electric stimulus to a selected location within the human body. Further, they can be used to monitor and make measurements for diagnostic tests of activities within the human body. Such catheters examine, diagnose and treat while positioned at a specific location inside the human body which is otherwise inaccessible without more invasive procedures. Recently, catheters have become more commonly used within the human heart and vascular system. In such use, the catheter is first inserted into a major vein or artery which is near the body surface and is then guided to the area for diagnosis or treatment by manipulating the catheter through the vessels of the body. As the utilization of catheters in remote and difficult to reach portions of the body including the heart has increased, it has become important to control precisely the movement of the catheter and its placement within the heart.

Control of the movement and placement of a catheter is difficult because of the inherent structure of the catheter. The body of conventional catheters is long and tubular. To provide sufficient control over the movement of the catheter, it is necessary that its structure be somewhat rigid. However, the catheters must not be so rigid as to prevent navigation of the catheter through the body vessel to arrive at the precise location where the medical procedure will be performed. In addition, it is important that the catheter not be so rigid as to cause damage to the body vessel through which it is being passed.

While it is important that the catheter not be so rigid as to cause injury to vessels and arteries, it is also important that there is sufficient rigidity in the catheter to accommodate torque control, i.e., the ability to transmit a twisting force along the length of the catheter. Sufficient torque control enables controlled maneuverability of the catheter by the application of a twisting force at the proximal end of the catheter that is transmitted along the catheter to its distal end. The requirement that existing catheters provide greater torque control often conflicts with the need for reduced rigidity to prevent injury.

As above stated, catheters are used increasingly for medical procedures involving the human heart. In these procedures, the catheter being used is typically guided to the heart through vessels including arteries, veins, and cardiac chambers and then it is placed at a precise location within the heart. Typically, the catheter is inserted in an artery or vein in the leg, neck, upper chest or arm of the patient and threaded, often with the aid of a guidewire, through various arteries and veins until the tip of the catheter reaches the desired location.

The distal portion of the catheter may be preformed into a desired curvature so that by torquing the catheter about its longitudinal axis, the catheter can be manipulated to the desired location within the heart. For example, U.S. Pat. No. 4,882,777 discloses a catheter with a complex curve at its distal end for specific procedures in the right ventricle of a human heart. In addition, there have been a number of catheters with a specialized curvature at its distal end designed for use in the coronary sinus, including U.S. Pat. Nos. 5,423,772, 5,549,581, 5,643,231, and 5,722,963.

While these catheters are particularly useful in the coronary sinus, each catheter is designed to be used for either a superior or an inferior approach to the coronary sinus, but not for both. In addition, the approach to the coronary sinus in some hearts is difficult because of the unusual anatomy of individual hearts. Further, entry into the coronary sinus is made more difficult because the right atrium of the heart is beating during the medical procedure.

To increase the ability of catheters to move and navigate within a human body, steerable catheters containing deflectable portions have been designed. Because these steerable catheters are deflectable, they can be used for medical procedures which require precise control over the orientation of the catheter tip, as shown, for example, in U.S. Pat. No. 5,728,828. With the devices disclosed in this patent, deflection of the catheter body is achieved by increasing or decreasing the axial compressive force on one side of the steerable tip by applying tension to, or removing tension from, the pull wire. By increasing the compressive force to one side of the tip, it is deflected in a predetermined direction.

U.S. Pat. No. 5,779,669 discloses a steerable catheter which includes a complexly curved section located proximal from the distal tip, designated by element 48 in FIG. 2. This complexly shaped steerable catheter is designed for utilization within the right atrium of the heart for ablation procedures against the outer wall of the right atrium, as shown, for example, in FIG. 8.

To control the movement of the distal portion of these catheters, control handles have been attached at the proximal end of the catheter body. For example, U.S. Pat. No. 5,395,329 describes a device useful for controlling the movement of steerable catheters. However, none of these steerable catheters have been specifically designed for usage in the coronary sinus and none in particular for usage for an inferior approach to the coronary sinus.

Accordingly, it is an object of this invention to prepare a steerable catheter designed for ease of access into the coronary sinus.

Another object of this invention is a steerable catheter for use in the coronary sinus which contains a fixed curve at its distal end.

Another object of the invention is a steerable catheter for use in the coronary sinus which contains a fixed curve at its distal end which curve is curved out of a plane formed by the remainder of the steerable catheter.

Another object of the invention is a steerable coronary sinus catheter which can perform electrophysiological sensing procedures from various locations within the coronary sinus.

It is a still further object of this invention to provide a fixed shape, steerable coronary sinus catheter which can sense electrical activity in and/or deliver electrical energy to the right and left atria as well as the left ventricle.

It is a still further object of this invention to provide a fixed shape steerable coronary sinus catheter which can approach the coronary sinus using either a superior or inferior approach.

These and other objects are obtained by the design of the steerable coronary sinus catheter of the instant invention.

SUMMARY OF INVENTION

The present invention is a steerable catheter specifically designed for use in the coronary sinus of the human heart which includes a precurved, flexible catheter body having a proximal and distal end containing a lumen, and a steerable catheter handle secured to the proximal end of the catheter body, wherein the catheter body includes a generally straight proximal section, a deflectable distal section and a precurved tip portion. In a preferred embodiment the precurved tip portion is formed in the shape of a hook, sized and shaped for facilitating entry of the catheter into the ostium of the coronary sinus wherein the hook portion is preferably curved out of a plane formed by the remaining portion of the catheter. Preferably, this precurved tip portion extends through an arc from about 45 to about 90 degrees and is curved out of the plane of the remaining portion of the catheter at least about 10 degrees and preferably from about 20 degrees to about 50 degrees.

In a further preferred embodiment the deflectable distal section is deflectable through an arc from about −15 degrees to about 180 degrees.

While the present catheter is designed for use in the coronary sinus, it is certainly not limited to that application but can be used for other procedures in the heart and in other locations within the body. Further, the catheter's use is certainly not limited to electrophysiological diagnostic applications but can be used for interventional pacing, defibrillation, ablation, cardioversion and other such cardiac procedures.

DETAILED DESCRIPTION

A steerable coronary sinus catheter (10) in accordance with this invention is provided for obtaining access to and maintaining precise placement and continuous electrical contact within the coronary sinus of the heart.

Increasingly, procedures have been designed to investigate, analyze and diagnose the causes of arrhythmia that occur in the heart. Normal contraction and relaxation of the heart muscle takes place as electrochemical signals pass sequentially through the myocardium from the atria to the ventricular tissue along a well defined route including the His-Purkinje System. The signal originates at a site called the sinus node in the right atrium. Methods to diagnose the cause of certain arrhythmia include connection of a patient to patch leads placed on the chest of the patient to record the electrical activity of the heart. However, more specific information with regard to the patient's arrhythmia can be gained by placing diagnostic electrophysiology catheters with sensing electrodes at specific locations in the heart. Once these electrodes are in a predetermined location within the heart, readings can be taken which will help determine the type of arrhythmia and diagnose the problems of the patient's heart. Examples of location for the placement of these catheters include designated points within the right atrium, the right ventricle, near the bundle of the His and, especially when information is desired from the left side of the heart, in the coronary sinus.

The coronary sinus is the largest cardiac vein which serves as a venous conduit from smaller veins within the myocardium to the right atrium. The coronary sinus extends from an opening for the coronary sinus in the right atrium, along the posterior of the heart to the left side of the heart along the atrioventricular border. When an electrophysiology catheter is placed in the coronary sinus, intracardiac electrograms may be obtained from the left atrium as well as the left ventricle if proper contact is made with designated locations in the heart. In addition, if electrodes are placed on the catheter outside of the coronary sinus, electrograms may be obtained of activity within the right atrium and even from the right ventricle. The location of the electrodes and the size, shape and location on the catheter may vary depending on the needs of the physician and the specific procedures for which the catheter is utilized.

Figure 1:
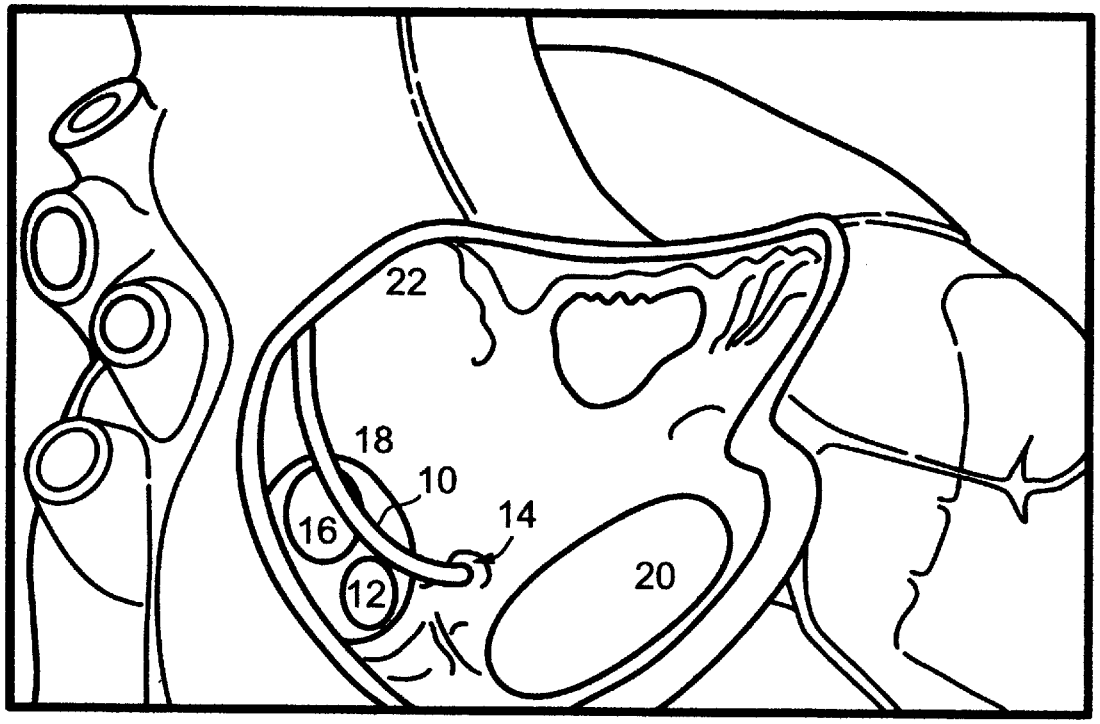
FIG. 1 is a cut away view of the human heart, specifically the right atrium, illustrating the relative location, for example, of the inferior vena cava, fossa ovalis, superior vena cava, valve of the coronary sinus and the ostium of the coronary sinus.

To understand the use of the steerable catheter (10) of the invention, it is first important to review the structure of the human heart as shown in FIG. 1. A typical human heart contains four chambers, a right and left atrium and right and left ventricle. The right atrium of the heart receives blood returning to the heart through the inferior vena cava (12) and superior vena cava (22). Adjacent to the opening in the right atrium of the inferior vena cava (12) is the ostium (14) of the coronary sinus. A tissue fold or primitive valve covers the coronary sinus ostium (14) to prevent blood from backflowing into the coronary sinus as it is being pumped out of the right atrium. This coronary sinus ostium (14) is a compliant semi-circular fold comprised of lining membrane of the right atrium. Within the right atrium generally, and above the coronary sinus ostium (14), is an oval depression called the fossa ovalis (16). Between the inferior vena cava (12) and the coronary sinus ostium (14) is also the eustachian ridge (18). The precise location of each of these elements may vary from patient to patient.

One of the difficulties in performing procedures within the coronary sinus is finding the ostium (14) to the coronary sinus while the heart is beating. Two approaches have been used for placement of an electrophysiology catheter within the coronary sinus, an inferior approach from below the heart through the inferior vena cava (12) and a superior approach from above the heart through the superior vena cava (22). In the inferior approach a catheter is advanced through the femoral vein through the inferior vena cava (12) into the right atrium. The tip of the catheter is then curved to aim it toward the ostium (14) of the coronary sinus. In the superior approach, a catheter is advanced through either the internal jugular or subclavian vein down through the superior vena cava (22) into the right atrium until it is directed toward the ostium (14) of the coronary sinus.

Gaining access to the ostium (14) of the coronary sinus is a very difficult procedure because of the anatomical structures within the right atrium which can be easily confused with the ostium (14) of the coronary sinus. Further, these features of the heart do not show up well on a fluoroscope, thus making the procedure quite difficult and time consuming for the physician.

The steerable catheter (10) of the present invention is specifically configured to avoid these problems by its placement in the right atrium at a position adjacent to the coronary sinus ostium (14) especially using an inferior approach. To assist in proper placement, the steerable catheter (10) of the present invention has a predetermined, precurved shape for its precurved tip portion (30) which permits it to be easily manipulated into the coronary sinus os (14). In addition, the curvature of this precurved tip portion (30) of the steerable catheter (10) permits important electrophysiological readings to occur while the precurved tip portion (30) of the steerable catheter (10) is present within the coronary sinus, including analysis of both the right and left atrium and the left ventricle.

Figures 2, 3:
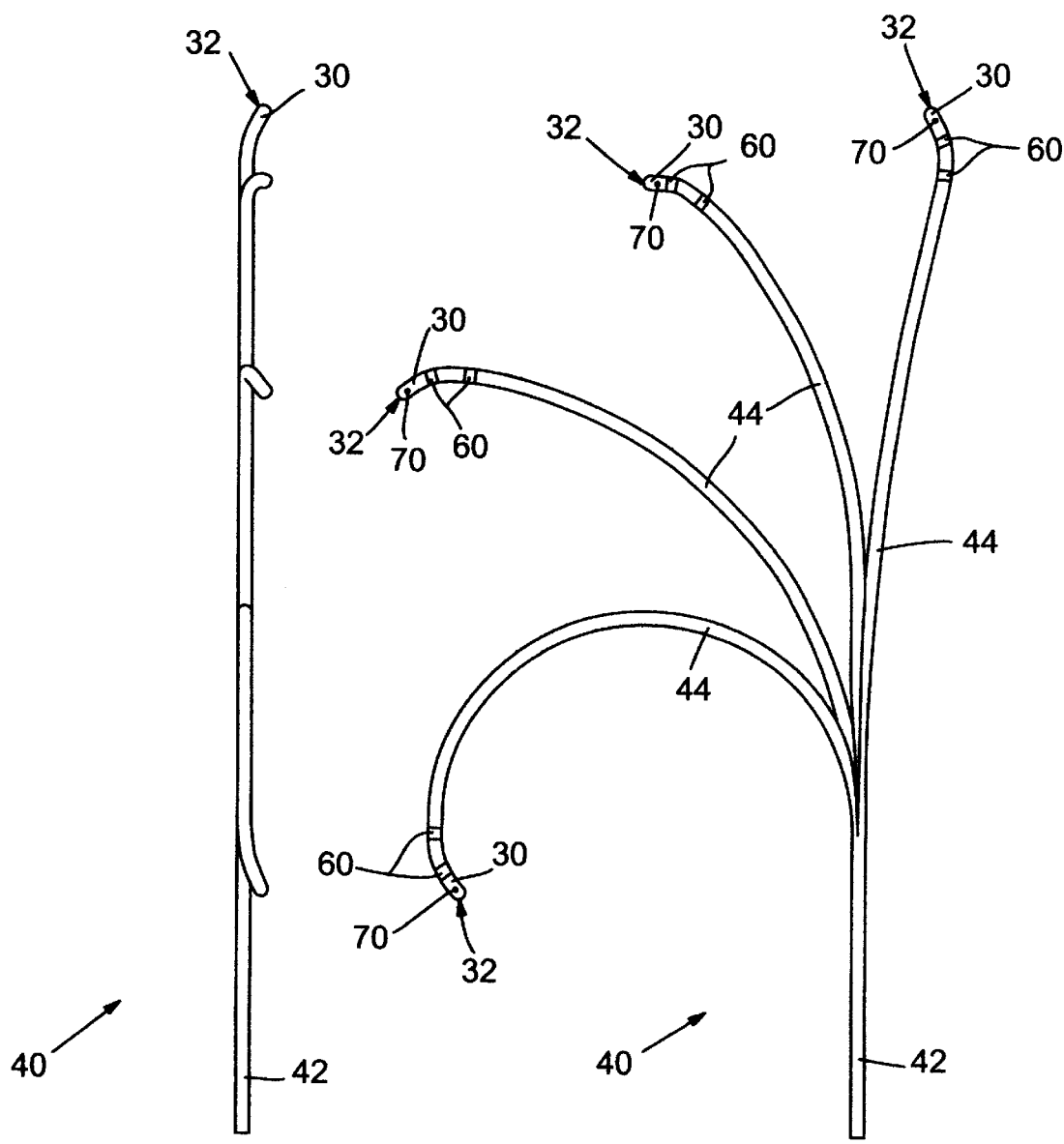
FIG. 2 is a side view of the steerable coronary sinus catheter with the deflectable distal section deflected in four separate positions of about −15 degrees, 35 degrees, 65 degrees and 180 degrees.
FIG. 3 is a front view of each of the embodiments of the steerable coronary sinus catheter of FIG. 2.
Figure 4:
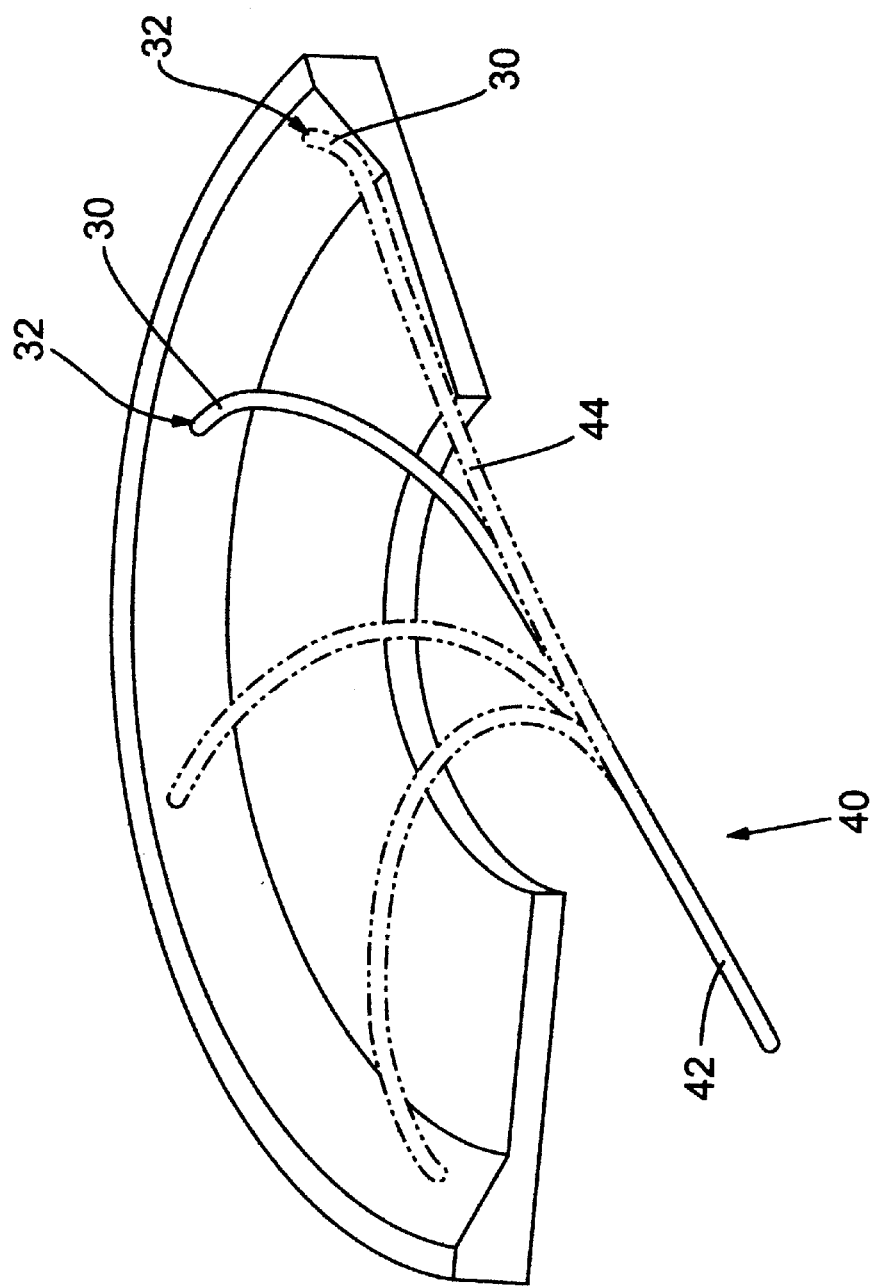
FIG. 4 is a side perspective view of the steerable coronary sinus catheter of FIG. 2 with the deflectable distal section deflected at the positions shown in FIG. 2 to show the out-of-plane deflection of the hook curve portion.
Figure 5:
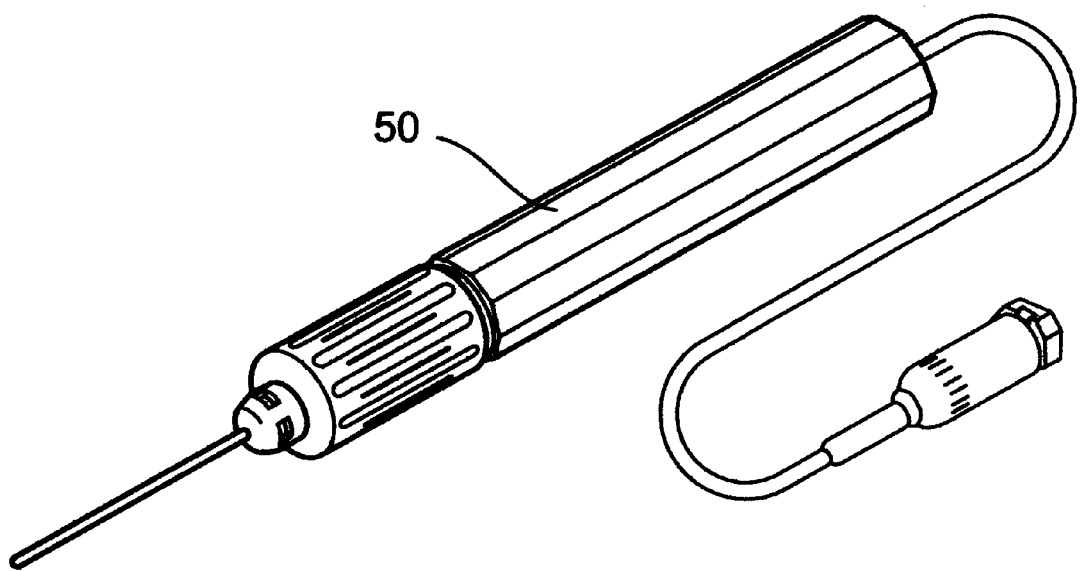
FIG. 5 is the steerable catheter handle of the steerable coronary sinus catheter.

As shown in FIGS. 2, 3, 4 and 5, in one preferred embodiment the steerable catheter (10) is comprised of two major components. The first is the catheter body (40) as shown in FIGS. 2, 3 and 4 which is secured to, and the movement of which is controlled by, the second portion, the steerable catheter handle (50) as shown in FIG. 5. The catheter body (40) includes a generally straight proximal section (42), a deflectable distal section (44) and the precurved tip portion (30) secured to the distal end of the deflectable distal section (44).

The steerable catheter handle (50) can be any conventional steerable handle for use with a catheter body (40) which acts by means of a pull wire (not shown) to bend a portion of the catheter body (40). In one preferred embodiment, the steerable catheter handle (50) is the steerable handle disclosed in U.S. Pat. No. 5,395,329, which patent is incorporated herein by reference. While the catheter handle of U.S. Pat. No. 5,395,329 is the preferred handle, other conventional steerable handles which contain components which bend or deflect portions of the catheter body (40) are also included in the disclosure of the present invention.

In the preferred steerable catheter (10), the pull wire, preferably made of metal, extends from the steerable catheter handle (50) through a lumen in the catheter body (40) to the deflectable distal section (44) of the catheter body (40). The pull wire is fixedly attached within the catheter body (40) at the location where bending or curving of the catheter body (40) is desired. The pull wire is preferably surrounded by a fluoro-type polymer sheath or the like for lubricity to keep the pull wire generally coaxial within the catheter body. The structure for attaching the pull wire within the lumen in the catheter body (40) is conventional and can be accomplished by any known procedures in the industry, such as fitting the distal end of the pull wire within the catheter body (40) and crimping it securely or welding it in place.

Electrical electrode wires (not shown) extend from the steerable catheter handle (50) through one or more of the lumen of the catheter body (40) to the location within the catheter body (40) where they are secured to electrodes (60) secured to the outside of the catheter body (40) as shown in FIG. 2. Some or all of the electrical electrode wires extend to the precurved tip portion (30) for attachment to electrodes (60) located there. However, some of the electrical electrode wires may extend to electrodes (60) located in the deflectable distal section (44) or even at a location proximal to that deflectable distal section (44).

The catheter body (40) is secured to the distal end of the steerable catheter handle (50) and includes the generally straight proximal section (42), the deflectable distal section (44) and the precurved tip portion (30), which is located at the distal end of the deflectable distal section (44). In one preferred embodiment, the generally straight proximal section (42) of the catheter body (40) is less pliable than the deflectable distal section (44) or the precurved tip portion (30). This decrease in pliability can be achieved through conventional procedures well known in the industry. For example, the generally straight proximal section (42) can be formed of any conventional catheter material having "memory" or permitting distortion from and subsequent substantial return to, the desired shape. In addition, to reenforce this generally straight proximal section (42), a reinforcing braid or other such suitable strand material having high tensile strength may be wound around the length of the generally straight proximal section (42) or incorporated into that portion of the catheter body (40). Suitable reinforcing braid may be prepared from materials such as stainless steel, aramids sold under the trademark registration, "KEVLAR," by E. I. Dupont and nickel chromium alloys.

The deflectable distal section (44) includes within a lumen the distal end of the pull wire. The structure of the deflectable distal section (44) is designed to permit its deflection upon the placement of tension on the pull wire or the removal of tension from the pull wire by manipulation of the steerable catheter handle (50). The composition of this deflectable distal section (44) is any conventional catheter material which can be deflected by the pull wire. Because this deflectable distal section (44) of the catheter body (40) is subject to being placed under tension and removed from tension by the elongated pull wire, it is preferably more pliable than the generally straight proximal section (42).

The location of the merger point between the generally straight proximal section (42) and the deflectable distal section (44) can be at any location that permits it to be utilized to advance the precurved tip portion (30) into the coronary sinus. In one preferred embodiment, this junction is from about 5 cm. (2 in.) to about 18 cm. (7 in.) and preferably from about 7.6 cm. (3 in.) to about 15 cm. (6 in.) from the distal end (32) of the precurved tip portion (30).

The length of the generally straight proximal section (42) of the catheter body (40) is from about 80 cm. (30 in.) to about 110 cm. (43 in.) with the length of the deflectable distal section from about 5 cm. (2 in.) to about 17 cm. (7 in.) and the length of the precurved tip portion (30) is from about 2 cm. (0.78 in.) to about 5 cm. (2 in.) in length.

The precurved tip portion (30) located at the distal end of the deflectable distal section (42) preferably contains a single precurved longitudinal curve or "hook curve." This precurved tip portion or hook curve (30) has a radius greater than about 0.5 cm. (0.1 in.) preferably from about 0.5 cm. (0.2 in.) to about 2.0 cm. (0.8 in.) and most preferably from about 0.5 cm. (0.2 in.) to about 1.5 cm. (0.6 in.). This hook curve (30) extends through an arc from about 45 to about 90 degrees, preferably from about 50 to about 70 degrees and most preferably about 60 degrees. Preferably, this hook curve (30) curves out of a plane formed by the remaining portion of the elongated catheter body (40) at least about 10 degrees as shown in FIGS. 3 and 4 and preferably from about 20 degrees to about 50 degrees. This structure permits access to the coronary sinus from an inferior approach using the brachial or femoral vein.

The deflectable distal section (44) is deflectable as shown in FIG. 2 at least about −15 degrees through an arc to a position of at least about 180 degrees. This ability to deflect allows the shape of the deflectable distal section (44) to be modified to permit the hook curve (30) to be moved within a wide range of locations in relation to the remaining portion of the catheter body (40). Notwithstanding, the embodiment which is deflected from about 30 degrees to about 60 degrees may be the most useful for access to the coronary sinus.

The steerable catheter (10) of the present invention is designed to supplement the catheters disclosed and claimed in U.S. Pat. Nos. 5,643,231, 5,549,581 and 5,423,772. Each of the catheters disclosed in these patents has both a first preformed curve and a second or hook curve. The curvatures that can be formed by the deflectable distal section (44) of the steerable catheter (10) of the invention include the curvature of the first preformed curve of these catheters disclosed in the above patents. In those patents, this first curvature curved through an arc of about 30 to about 50 degrees. Because the deflectable distal section (44) can be deflected through an arc ranging from about +180 degrees to about −15 degrees as shown in FIG. 2, this deflectable distal section (44) can be formed with the same curvature as the first curve of the catheter of these patents for use in a superior or inferior approaches to the coronary sinus os (14). However, it also can be modified to form a wide range of other curves. This flexibility in available curvature is especially important as the inferior approach to the coronary sinus os (14) requires a greater curvature of the deflectable distal portion (44) than does the superior approach.

Distal from the deflectable distal section (44) of the catheter body (10) is the precurved tip portion (30). This tip portion (30) is formed from conventional catheter material.

The precurved tip portion (30) is preformed in a curved shape, and generally maintains that curved shape during the entire medical procedure. However, the extent of the curvature of this tip portion (30) may be reduced somewhat if a significant curvature is placed on the deflectable distal section (44) of the steerable catheter (10) by the pull wires. The curvature of the precurved tip portion (30) is preferably formed by securing within a lumen (not shown) within the precurved tip portion (30) stiffening material, which material forces the precurved tip portion (30) to maintain is curved shape throughout the medical procedure.

The hook curve (30) also serves to limit partially the depth to which the distal end (32) of the hook curve (30) can be inserted into the coronary sinus.

For the purpose of illustration and not limitation, the diameter of the catheter body (40) may vary from about 3.0 to about 8.0 "French" units (one "French" equals about one-third of a millimeter).

Toward the distal end (32) of the tip portion (30) of the catheter body (40) are placed a plurality of electrodes (60), preferably at least two with one of those at the tip (32). See FIG. 2. The number of electrodes (60) and their placement on the catheter body (40) depends on the intended usage for the steerable catheter (10). The ultimate number of electrodes (60) may be as many as 10 or more electrodes (60). In one preferred embodiment, one or more electrodes (60) are placed near or at the tip (32) of the catheter body (40) and one or more are placed on the deflectable distal section (44).

By this placement, when the tip portion (30) of the steerable catheter (10) of the present invention is placed within the coronary sinus os (14) for sensing purposes, the catheter (10) is able to sense both sides of the heart at the same time.

If appropriate to the intended use, a lumen (not shown) may also be incorporated into the catheter for infusion of fluids or withdrawal of blood samples. The diameter of the lumen should be sufficient to accomplish the intended use within the catheter (10). In this embodiment one or a plurality of vents (70) are also located near the distal tip (32) of the catheter body (40) as shown in FIG. 2, with the precise location and number depending on the intended use for the catheter (10).

In operation, the steerable coronary sinus catheter (10) as described in the present invention containing electrodes (60) from 2 to about 10 connected to electrophysiology sensing devices in one embodiment using a superior approach is inserted percutaneously through the internal jugular vein or the subclavian vein and advanced under fluoroscopic control through the superior vena cava (22) to the right atrium. In another preferred embodiment the distal tip (32) is introduced into the brachial vein or femoral vein using an inferior approach through the inferior vena cava (12) into the right atrium. The precurved tip portion (30) of the steerable coronary sinus catheter (10) is then directed across the right atrium by the steerable handle and pull wire until it contacts the ostium (14) of the coronary sinus. The specific curvature of the precurved tip portion (30) along with the ability to vary the curvature of the deflectable distal section (44), permits ease in placing the precurved tip portion (30) of the steerable catheter (10) within the ostium (14) of the coronary sinus using either approach. Under fluoroscopic guidance the steerable catheter (10) is advanced until it is inserted into the coronary sinus os (14) where it is advanced as far as is required or desired. Continuous and stable recordings of the electrical pathways running near the coronary sinus can then be produced. As a result of the unique curvature of the precurved distal portion (30) of the steerable coronary sinus catheter (10), as well as the unique structure of the steerable catheter (10), it is relatively easy to locate the ostium (12) of the coronary sinus and, in addition, take electrophysiology readings within the coronary sinus. In this fashion the time and x-ray exposure required during the procedure can be reduced.

In addition to the use for the coronary sinus catheter (10) as a diagnostic electrophysiology steerable catheter (10), it may also be used for other medical procedures within the coronary sinus. For example, by modifying the mode of the use for the electrodes (60) of the steerable catheter (10), the types of medical instruments to which the proximal end of the catheter is attached, the steerable catheter (10) can also serve as a means for interventional pacing or permanent pacing of the heart. Pacing using the coronary sinus catheter (10) will also provide the ability to pace the left atrium. By the administration of a controlled amount of electrical energy to the heart, which is at that time experiencing an arrhythmia, the steerable coronary sinus catheter (10) may also be used for defibrillation purposes or for cardioversion. Other uses well known in the industry are also included within the description of the invention.

While it is apparent from the foregoing that particular forms of the invention have been illustrated and described, various modifications can be made without departing from the spirit and scope of the invention. Accordingly, it is not intended that the invention be limited except by the appended claims.

I claim:

1. A steerable catheter for insertion into the coronary sinus through the ostium of the coronary sinus comprising a flexible catheter body having proximal and distal ends containing a lumen; and a steerable catheter handle secured to the proximal end of the catheter body capable of deflecting a portion of the catheter body;

wherein the catheter body comprises a generally straight proximal section, a deflectable distal section and a precurved tip portion distal from the deflectable distal section located at the distal end of the catheter body.

2. The steerable catheter of claim 1 wherein the deflectable distal portion is deflectable by the steerable catheter handle to form a shape which places the precurved tip portion adjacent to the ostium of the coronary sinus.

3. The steerable catheter of claim 1 wherein the precurved tip portion is curved in the shape of a hook, sized and shaped for facilitating entry into the ostium of the coronary sinus.

4. The catheter of claim 1, wherein the precurved tip portion comprises a hook curve having a radius of curvature of less than about 2.0 cm. (0.8 in.).

5. The catheter of claim 4, wherein the hook curve has a radius of curvature of greater than about 0.5 cm. (0.2 in.).

6. The catheter of claim 4, wherein the hook curve extends through an arc greater than about 45 degrees.

7. The catheter of claim 4, wherein the hook curve extends through an arc less than about 90 degrees.

8. The catheter of claim 1, wherein the deflectable distal section is capable of being deflected to form a first curve extending through an arc greater than about 10 degrees.

9. The catheter of claim 8, wherein the first curve is capable of being deflectable to form a first curve which extends through an arc of less than about 180 degrees.

10. The catheter of claim 8, wherein the deflectable distal section is capable of being deflected to form a first curve, wherein the tip portion comprises a hook curve, and wherein the first and hook curves are capable of being curved in the same general direction.

11. The catheter of claim 8 wherein a combination of the straight proximal portion and the deflectable distal portion when deflected to form a first curve from a plane and wherein the hook curve curves out of the plane formed by the straight proximal portion and the deflectable distal section at least about 10 degrees.

12. The catheter of claim 8 wherein a combination of the straight proximal portion and the deflectable distal portion when deflected to form a first curve form a plane and wherein the hook curve curves out of the plane formed by the straight proximal portion and the deflectable distal section at least about 20 degrees to about 50 degrees.

13. The catheter of claim 1, wherein the precurved tip portion is more pliable than the deflectable distal section.

14. The catheter of claim 1 wherein the straight proximal section is reinforced with reinforcing material.

15. The catheter of claim 1, wherein at least one electrode is placed on the precurved tip portion.

16. The catheter of claim 1, further comprising a vent located in the precurved tip portion.

* * * * *